United States Patent
Sing et al.

(10) Patent No.: US 8,620,625 B2
(45) Date of Patent: Dec. 31, 2013

(54) ABOVE BED SENSOR

(75) Inventors: Jack Barney Sing, Batesville, IN (US); Michael M. Frondorf, Lakeside Park, KY (US)

(73) Assignee: Hill-Rom Services, Inc., Batesville, IN (US)

( * ) Notice: Subject to any disclaimer, the term of this patent is extended or adjusted under 35 U.S.C. 154(b) by 451 days.

(21) Appl. No.: 12/847,337

(22) Filed: Jul. 30, 2010

(65) Prior Publication Data

US 2012/0029879 A1 Feb. 2, 2012

(51) Int. Cl.
*H03F 1/26* (2006.01)
*A47B 71/00* (2006.01)
*G01V 8/00* (2006.01)

(52) U.S. Cl.
USPC .......................... 702/189; 5/600; 250/559.39

(58) Field of Classification Search
USPC ......... 702/189, 57, 65, 81, 84, 127, 150–153, 702/159, 172, 175, 188, 190, 193; 340/540–541, 545.3, 551–552, 573.1, 340/600; 5/600, 611; 250/559.29, 559.3, 250/559.32, 559.35–559.36, 559.39, 559.4; 700/9, 13
See application file for complete search history.

(56) References Cited

U.S. PATENT DOCUMENTS

| | | | |
|---|---|---|---|
| 1,388,242 A | 8/1921 | Dodds | 5/610 |
| 2,592,166 A | 4/1952 | McLean et al. | 5/611 |
| 2,604,639 A | 7/1952 | Killifer | 5/611 |
| 3,039,118 A | 6/1962 | Hutt | 5/611 |
| 3,919,727 A | 11/1975 | Paine | 5/611 |
| 3,972,320 A | 8/1976 | Kalman | 600/519 |
| 4,057,240 A | 11/1977 | Damico et al. | 5/611 |
| 4,087,872 A | 5/1978 | Smirle | 5/611 |
| 4,152,795 A | 5/1979 | Rodosta et al. | 5/658 |
| 4,196,425 A | 4/1980 | Williams, Jr. et al. | 340/573.4 |
| 4,539,560 A | 9/1985 | Fleck et al. | 340/573.4 |
| 4,633,237 A | 12/1986 | Tucknott et al. | 340/573.4 |
| 4,814,751 A | 3/1989 | Hawkins et al. | 340/573.4 |
| 4,837,877 A | 6/1989 | Hamada et al. | 5/10.2 |
| 4,907,845 A | 3/1990 | Wood | 340/573.4 |
| 4,947,152 A | 8/1990 | Hodges | 340/573.4 |
| 4,952,928 A | 8/1990 | Carroll et al. | 340/10.41 |
| 5,008,654 A | 4/1991 | Callaway | 340/573.1 |
| 5,095,560 A | 3/1992 | Volker | 5/11 |

(Continued)

FOREIGN PATENT DOCUMENTS

| | | |
|---|---|---|
| WO | WO 2006/011124 | 2/2006 |
| WO | WO 2006/117788 | 11/2006 |

OTHER PUBLICATIONS

Aoki et al., Study on Respiration Monitoring Method Using Near-Infrared Multiple Slit-Lights Projection, Nov. 7-9, 2005, International Symposium on Micro-NanoMechatronics and Human Science, 2005 IEEE, 6 pp.*
Abstract of Aoki et al. reference, Feb. 27, 2013, 2 pp.*

*Primary Examiner* — Toan Le
(74) *Attorney, Agent, or Firm* — Barnes & Thornburg LLP

(57) ABSTRACT

A monitoring system for monitoring a patient in a patient-support apparatus includes a detector, a standard, and a controller. The detector detects electromagnetic radiation in a field. The standard conveys a predetermined electromagnetic signature to the detector. The controller monitors the electromagnetic radiation in the field and compares the electromagnetic radiation to the standard to determine the position of a patient supported on a patient-support apparatus positioned in the field.

20 Claims, 4 Drawing Sheets

(56) References Cited

U.S. PATENT DOCUMENTS

| | | | |
|---|---|---|---|
| 5,107,845 A | 4/1992 | Guern et al. | 600/473 |
| 5,218,344 A | 6/1993 | Ricketts | 340/573.4 |
| 5,276,432 A | 1/1994 | Travis | 40/573.4 |
| 5,353,012 A | 10/1994 | Barham et al. | 340/573.4 |
| 5,365,217 A | 11/1994 | Toner | 340/539.11 |
| 5,416,695 A | 5/1995 | Stutman et al. | 600/300 |
| 5,490,298 A | 2/1996 | Goldsmith et al. | 5/611 |
| 5,495,288 A | 2/1996 | Broady et al. | 348/155 |
| 5,519,380 A | 5/1996 | Edwards | 340/573.4 |
| 5,583,758 A | 12/1996 | McIlroy et al. | 705/2 |
| 5,633,627 A | 5/1997 | Newham | 340/573.4 |
| 5,650,770 A | 7/1997 | Schlager et al. | 340/573.4 |
| 5,714,931 A | 2/1998 | Petite et al. | 340/539.17 |
| 5,732,401 A | 3/1998 | Conway | 705/29 |
| 5,738,102 A | 4/1998 | Lemelson | 600/483 |
| 5,740,800 A | 4/1998 | Hendrickson et al. | 600/300 |
| 5,765,139 A | 6/1998 | Bondy | 705/7.24 |
| 5,780,798 A | 7/1998 | Hall-Jackson | 200/85 R |
| 5,781,442 A | 7/1998 | Engleson et al. | 700/214 |
| 5,831,669 A | 11/1998 | Adrain | 348/143 |
| 5,844,488 A | 12/1998 | Musick | 340/573.4 |
| 5,877,675 A | 3/1999 | Rebstock et al. | 340/286.07 |
| 5,941,836 A | 8/1999 | Friedman | 600/595 |
| 5,946,659 A | 8/1999 | Lancelot et al. | 705/3 |
| 5,953,704 A | 9/1999 | McIlroy et al. | 705/2 |
| 6,049,281 A | 4/2000 | Osterweil | 340/573.4 |
| 6,067,019 A | 5/2000 | Scott | 340/573.4 |
| 6,078,261 A | 6/2000 | Davsko | 340/573.4 |
| 6,104,295 A | 8/2000 | Gaisser et al. | 340/573.4 |
| 6,125,350 A | 9/2000 | Dirbas | 705/2 |
| 6,154,139 A | 11/2000 | Heller | 340/573.4 |
| 6,160,478 A | 12/2000 | Jacobsen et al. | 340/539.12 |
| 6,169,484 B1 | 1/2001 | Schuchman et al. | 340/573.1 |
| 6,204,767 B1 | 3/2001 | Sparks | 340/573.1 |
| 6,259,355 B1 | 7/2001 | Chaco et al. | 340/286.07 |
| 6,402,691 B1 | 6/2002 | Peddicord et al. | 600/300 |
| 6,433,690 B2 | 8/2002 | Petelenz et al. | 340/573.1 |
| 6,466,125 B1 | 10/2002 | Richards et al. | 340/573.4 |
| 6,524,239 B1 | 2/2003 | Reed et al. | 600/300 |
| 6,583,727 B2 | 6/2003 | Nunome | 340/665 |
| 6,611,206 B2 | 8/2003 | Eishelman et al. | 340/573.1 |
| 6,611,783 B2 | 8/2003 | Kelly, Jr. et al. | 702/150 |
| 6,624,754 B1 | 9/2003 | Hoffman et al. | 340/573.1 |
| 6,640,212 B1 | 10/2003 | Rosse | 705/7.13 |
| 6,674,403 B2 | 1/2004 | Gray et al. | 342/463 |
| 6,748,250 B1 | 6/2004 | Berman et al. | 600/310 |
| 6,753,783 B2 | 6/2004 | Friedman et al. | 340/573.7 |
| 6,788,206 B1 | 9/2004 | Edwards | 340/573.1 |
| 6,791,460 B2 | 9/2004 | Dixon et al. | 340/573.1 |
| 6,804,656 B1 | 10/2004 | Rosenfled et al. | 705/3 |
| 6,821,258 B2 | 11/2004 | Reed et al. | 600/595 |
| 6,822,571 B2 | 11/2004 | Conway | 340/573.1 |
| 6,830,180 B2 | 12/2004 | Walsh | 235/385 |
| 6,838,992 B2 | 1/2005 | Tenarvitz | 340/573.1 |
| 6,876,303 B2 | 4/2005 | Reeder et al. | 340/573.1 |
| 6,897,781 B2 | 5/2005 | Cooper et al. | 340/573.1 |
| 6,900,732 B2 | 5/2005 | Richards | 340/573.1 |
| 6,909,367 B1 | 6/2005 | Wetmore | 340/539.21 |
| 6,915,170 B2 | 7/2005 | Engleson et al. | 700/2 |
| 6,941,239 B2 | 9/2005 | Unuma et al. | 700/141 |
| 6,958,706 B2 | 10/2005 | Chaco et al. | 340/870.11 |
| 6,968,294 B2 | 11/2005 | Gutta et al. | 702/188 |
| 6,975,230 B1 | 12/2005 | Brilman | 340/573.1 |
| 6,987,232 B2 | 1/2006 | Smith et al. | 200/85 R |
| 7,001,334 B2 | 2/2006 | Reed et al. | 600/300 |
| 7,035,432 B2 | 4/2006 | Szuba | 382/103 |
| 7,110,569 B2 | 9/2006 | Brodsky et al. | 382/103 |
| 7,198,320 B2 | 4/2007 | Rasmussen | 296/170 |
| 7,242,306 B2 | 7/2007 | Wildman et al. | 340/573.1 |
| 7,369,680 B2 | 5/2008 | Trajkovic et al. | 382/103 |
| 7,406,731 B2 | 8/2008 | Menkedick et al. | 5/618 |
| 7,452,336 B2 | 11/2008 | Thompson | 600/558 |
| 7,502,498 B2 | 3/2009 | Wen et al. | 382/128 |
| 7,505,620 B2 | 3/2009 | Braune et al. | 382/152 |
| 7,987,069 B2 | 7/2011 | Rodgers et al. | 702/150 |
| 2001/0044965 A1 | 11/2001 | Blevins | 5/611 |
| 2002/0046423 A1 | 4/2002 | Vilsmeier | 5/11 |
| 2002/0140559 A1 | 10/2002 | Zhou et al. | 340/573.1 |
| 2002/0165733 A1 | 11/2002 | Pulkkinen et al. | 705/2 |
| 2003/0013459 A1 | 1/2003 | Rankin et al. | 455/456.1 |
| 2003/0028399 A1 | 2/2003 | Davis et al. | 705/2 |
| 2003/0058111 A1 | 3/2003 | Lee et al. | 340/573.1 |
| 2003/0069815 A1 | 4/2003 | Eisenberg et al. | 5/7.13 |
| 2003/0167187 A1 | 9/2003 | Bua | 705/2 |
| 2003/0169171 A1 | 9/2003 | Strubbe et al. | 340/573.1 |
| 2004/0172290 A1 | 9/2004 | Leven | 705/2 |
| 2004/0193449 A1 | 9/2004 | Wildman et al. | 705/2 |
| 2005/0125899 A1 | 6/2005 | Hanson et al. | 5/613 |
| 2005/0190062 A1 | 9/2005 | Sullivan et al. | 340/573.1 |
| 2005/0240086 A1 | 10/2005 | Akay | 600/300 |
| 2005/0242946 A1 | 11/2005 | Hubbard, Jr. et al. | 340/539.12 |
| 2005/0251914 A1* | 11/2005 | Schaller et al. | 5/601 |
| 2005/0283382 A1 | 12/2005 | Donoghue et al. | 705/2 |
| 2006/0033625 A1 | 2/2006 | Johnson et al. | 482/8 |
| 2006/0053035 A1 | 3/2006 | Eisenberg | 705/2 |
| 2006/0056655 A1 | 3/2006 | Wen et al. | 382/103 |
| 2006/0265805 A1 | 11/2006 | Bellingroth | 5/11 |
| 2007/0033072 A1 | 2/2007 | Bildirici | 705/3 |
| 2007/0132597 A1 | 6/2007 | Rodgers | 340/573.1 |
| 2007/0157385 A1 | 7/2007 | Lemire et al. | 5/600 |
| 2007/0222599 A1 | 9/2007 | Coveley et al. | 340/572.4 |
| 2008/0272918 A1 | 11/2008 | Ingersoll | 340/573.1 |
| 2009/0044334 A1 | 2/2009 | Parsell et al. | 5/424 |
| 2009/0275808 A1* | 11/2009 | DiMaio et al. | 600/301 |

* cited by examiner

ABOVE BED SENSOR

BACKGROUND

The present disclosure is related to sensors for monitoring the position of a patient in a patient-support apparatus. More specifically, the present disclosure is related to monitoring patient movement in a patient-support apparatus with sensor that is spaced apart from the patient-support apparatus.

In a care environment such as a hospital, for example, the movement of patients is monitored for safety. For elderly patients and other patients who may be disoriented due to a medical condition or treatment, patient monitoring systems have been developed to alert a caregiver if the patient has exited their bed. In some instances, a sensor mat is used to determine the presence of the patient. Additional development of hospital beds with integrated scale systems has also resulted in systems that monitor the sensed weight to determine if the patient had exited the bed, and if so, to signal to a nurse call system of that condition.

Further development has resulted in additional integrated systems to monitor the amount of patient movement and alert a caregiver if a patient has begun to move. These systems are useful in predicting that an at-risk patient may be attempting to leave their bed. It is also useful to determine when a patient who is asleep or under anesthesia has awakened. More recently, the lack of patient movement has been monitored to determine the risk of development of decubitus ulcers or bed sores on the patient's skin due to immobility.

Other sensors have been employed to detect movement of patients to determine sleep patterns, detect seizures, or to detect incontinence. Such sensors are generally supported on or near a patient-support apparatus with cords or wires connecting the sensors to independent control systems for each detection system. The cords and wires must then be disconnected when the patient-support apparatus is moved from the room. In addition, the cords and wires present trip hazards and wire management issues in the patient room.

SUMMARY

The present application discloses one or more of the features recited in the appended claims and/or the following features which, alone or in any combination, may comprise patentable subject matter:

According to one aspect of the present disclosure, a monitoring system for monitoring a patient in a patient-support apparatus comprises a detector, a standard, and a controller. The detector is operable to detect electromagnetic radiation within a detection field. The standard is positioned in the detection field and conveys electromagnetic radiation having a predetermined signature to the detector. The controller is coupled to the detector and includes a processor and a memory device coupled to the processor. The memory device includes instructions that, when executed by the processor, cause the controller to evaluate data received from the detector. The data received by the detector includes all of the electromagnetic radiation in the detection field. The electromagnetic radiation in the field is compared to the signature of the standard to determine if changes in the electromagnetic radiation are indicative of movement of a person in the detection field.

The memory device may also include instructions that, when executed by the processor, cause the controller to output a signal if the changes in the electromagnetic radiation are indicative that movement of a person in the detection field exceeds a threshold value. The signal may be output to a local alarm near the patient-support apparatus. In some embodiments, the system further includes a remote station that is spaced apart from the detection field and coupled to the controller, and wherein the signal is transmitted to the monitoring station. The local alarm or the remote station may each generate either a visual or an audible alarm. In some embodiments, both a visual and an audible alarm are generated.

In some embodiments the electromagnetic radiation detected by the detector is in the visible spectrum. In some embodiments the electromagnetic radiation detected by the detector is in the infra red spectrum. The system may further comprise a second detector operable to detect electromagnetic radiation within at least a portion of the detection field of the first detector. When present, the second detector is coupled to the controller. The memory device may further include instructions that, when executed by the processor, compare electromagnetic radiation received by the second detector to electromagnetic radiation received by the first detector and to the signature of the standard to determine if changes in the electromagnetic radiation detected by the first detector are indicative of movement of a person in the detection field. The memory device may further include instructions that, when executed by the processor, cause the controller to output a signal if the changes in the electromagnetic radiation sensed by both the first and second detector are indicative that movement of a person in the detection field exceeds a threshold value. The signal may be transmitted to the local alarm or the remote station. The controller may communicate wirelessly to the local alarm and the remote station, or the controller may have a hardwired connection to either the local alarm or the remote station.

The standard may be portable in some embodiments. The memory device may include instructions that, when executed by the processor, cause the system to determine a physical position of the portable standard. The physical position may define a datum and changes in the electromagnetic radiation detected by the detector may be compared to the datum to determine if the changes in the electromagnetic radiation are indicative of movement of a patient on the patient-support apparatus.

In some embodiments, the signature of the standard defines a datum and the system evaluates changes in electromagnetic radiation relative to the datum to determine if a patient on the patient-support apparatus has moved from an initial position.

In some embodiments, the system comprises a plurality of standards each having a predetermined signature. The memory device may include instructions that, when executed by the processor, cause the system to monitor changes in the position of each of the plurality of standards. The memory device may also include instructions that, when executed by the processor, cause the system to determine if one or more of the plurality of standards is in an unacceptable position. In some embodiments, the system generates a signal indicative of the unacceptable position and transmits the signal to a remote station spaced apart from the patient-support apparatus.

In some embodiments, the memory device includes instructions that, when executed by the processor, cause the system to evaluate the electromagnetic radiation to determine a location of a patient supported on the patient-support apparatus. The system may compare the location of the patient to the standards to determine if the patient is in an unacceptable position.

The position of the patient may be determined by determining a centroid of the patient. The centroid of the patient may be determined by weighting components of the thermal profile of the patient to determine a thermally weighted centroid.

According to another aspect of the present disclosure, a method of monitoring a position of patient in a patient-support apparatus includes monitoring electromagnetic radiation in a detection field, establishing a reference based on a standard in the detection field, and monitoring changes in the electromagnetic radiation in the detection field to determine if there is movement relative to the standard. The reference may be established based on a plurality of standards. The method may further include generating a notification if the movement relative to the standard exceeds a threshold. The notification may be generated proximate to the patient-support apparatus. The notification may be generated at a location spaced apart and separate from the patient-support apparatus. The position of the patient may be estimated by determining a centroid of the patient. The centroid of the patient may be determined by evaluating the thermal profile of the patient to determine a thermal centroid.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
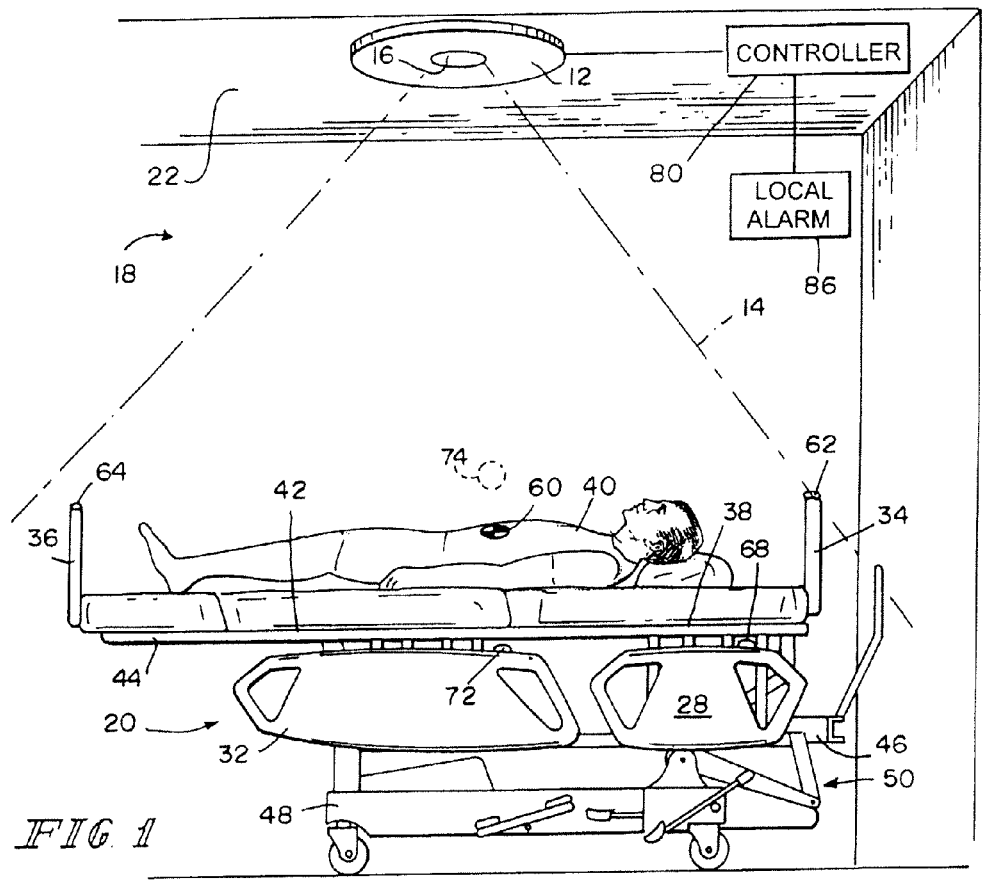
FIG. 1 is a perspective view of a patient supported in a supine position on a patient-support apparatus in hospital room with an sensor positioned above the patient-support apparatus such that the patient-support apparatus is positioned in the field of view of the sensor.

A patient monitoring system 10 includes a sensor 12 that is operable to detect electromagnetic radiation such as infrared radiation or light waves in the visible spectrum. The sensor 12 detects electromagnetic radiation in a field of view 14 which defines a detection zone. The electromagnetic radiation received by a detector 16 in the sensor 12 with optical elements such as lenses and filters as is well known in the art focusing the electromagnetic radiation. In the illustrative embodiment of FIG. 1, the sensor 12 is positioned on a ceiling 22 of a patient room 18. The detection zone 14 of the sensor 12 is positioned in a known location such that a patient-support apparatus 20 may be positioned in the patient room 18 so that the electromagnetic radiation in the area of the patient-support apparatus 20 is detected by the sensor 12.

Figure 2:
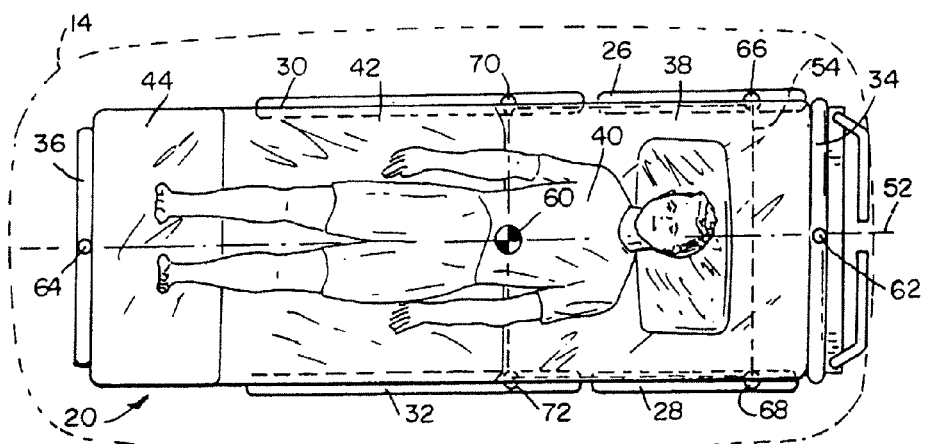
FIG. 2 is a top view of the patient-support apparatus of FIG. 1.

As shown in FIGS. 1 and 2, the patient-support apparatus 20 includes a number of barrier elements including a patient-right head siderail 26, a patient-left head siderail 28, a patient-right foot siderail 30, and a patient-left foot siderail 32. In addition, the patient-support apparatus may include a headpanel 34 and a footpanel 36. The patient-support apparatus 20 includes a number of support sections including an articulated head section 38 pivotable relative to an intermediate frame 46. An articulated thigh section 42 is also pivotable relative to the intermediate frame 46 and an articulated foot section 44 is pivotable relative to the thigh section 42. The support sections are supported on the intermediate frame 46 and the articulated sections 38, 40, 42. The intermediate frame 46 is supported above a base frame 48 and movable relative to the base frame 48 by a lift system 50 as is well known in the art.

A number of standards 62, 64, 66, 68, 70, and 72 are positioned on various elements of the patient-support apparatus 20 so that references points may be established on the patient-support apparatus 20. The standards 62, 64, 66, 68, 70, and 72 are configured to reflect a particular wavelength of light when illuminated so that the system 10 may identify the standards 62, 64, 66, 68, 70, and 72 by the reflected wavelength. In the alternative, the standards 62, 64, 66, 68, 70, and 72 may reflect widely varying wavelengths in a relatively small or clustered area such that the system 10 can discriminate the cluster of varying wavelengths from the environment in the patient room 18 to determine the location of a particular one of the standards 62, 64, 66, 68, 70, and 72. In still other embodiments, the standards 62, 64, 66, 68, 70, and 72 may be an electromagnetic radiation emitter that generates a particular radiation signature which may be discriminated by the system 10 to determine the position of the standards 62, 64, 66, 68, 70, and 72.

Referring now to FIG. 2, a first standard 62 is shown to be positioned on the headpanel 34 and a second standard 64 is positioned on the footpanel 36 with each of the standards 62 and 64 being centered on the respective panels. The standards 62 and 64 define a longitudinal axis 52 of the patient-support apparatus 20 which may be utilized by the system 10 when the system 10 is evaluating electromagnetic radiation in the field 14.

Figure 4:
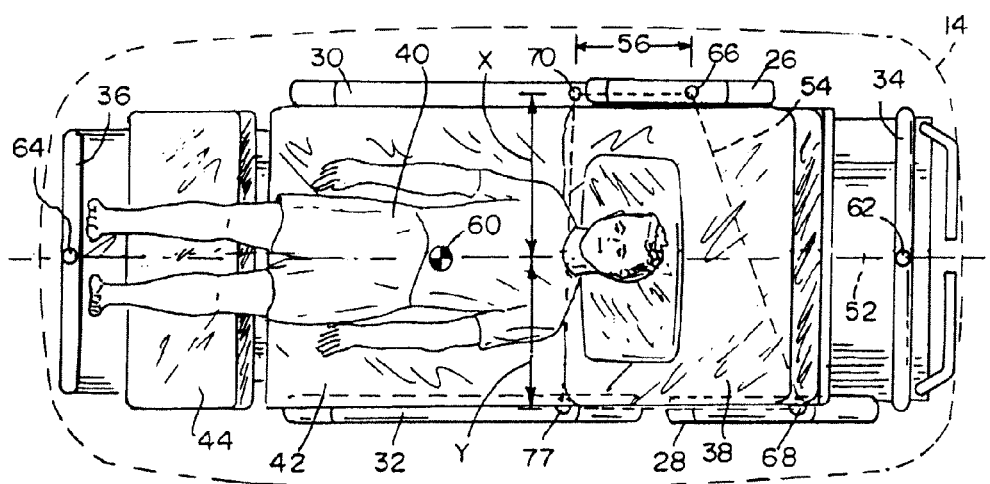
FIG. 4 is a top view of the patient-support apparatus in the position shown in FIG. 3.

The longitudinal axis 52 serves as a datum against which movement detected by the system 10 is compared to make determinations as to whether the detected movement exceeds a predetermined threshold or is of such a magnitude that it may be indicative of certain characteristics of the patient 40 supported on the patient-support apparatus 20. The standards 66, 68, 70, 72 form the vertices of a four sided polygon 54 that is detected by the system 10. The position of the patient 40 supported on the patient-support apparatus 20 may also be compared to the polygon 54 to determine if the patient 40 is outside of an acceptable position on the patient-support apparatus 20. In addition, the standards 66, 68, 70, 72 also allow the system 10 to determine if the respective side rails 26, 28, 30, 32 are in a raised or lowered position. In the illustrative embodiment of the present disclosure, the side rails 26, 28, 30, 32 are spaced laterally inwardly toward the axis 52 when the side rails are in a lowered position as compared to the lateral position in a raised position. Referring now to FIG. 4, it can be seen that the side rails 26, 30 on the patient right side of the patient-support apparatus 20, which are in a raised position, are positioned such that the standards 66, 70 positioned on the side rails 26, 30 respectively, are spaced away from the longitudinal axis 52 by a distance X. In contrast, the side rails 28, 32 on the patient left side of the patient-support apparatus 20, which are in a lowered position, results in the standards 68, 72 being spaced away from the longitudinal axis 52 by a distance Y which is less than X. The system 10 compares the positions of the standards on the respective side rails to the longitudinal axis 52 to determine if each of the side rails is in a raised or lowered position.

In the illustrative embodiment, the polygon 54 is detected from an overhead position. Because the head and side rails 26, 28 move with the head section 38, while the foot side rails 30, 32 are fixed to the intermediate frame 46, raising of the head section 38 results in a change in the dimensions of the polygon 54 as viewed by the sensor 12. Comparing the polygon 54 in FIG. 4 to the polygon 54 in FIG. 5, it can be seen that when the head section 38 is raised as in FIG. 4, a length dimension 56 of the polygon 54 is reduced. By monitoring the changes in the position of the standards and changes in the dimensions between the standards, the system 10 is able to discern changes in the position of the sections 38, 40, 42, 44 and frames 46, 48 of the patient-support apparatus 20. Comparing the information concerned about the position of the patient-support apparatus 20 members, to a detected position of a patient 40 supported on the patient-support apparatus 20, the system can determine if the patient 40 is moving or is out of acceptable position on the patient-support apparatus 20.

Figure 6:
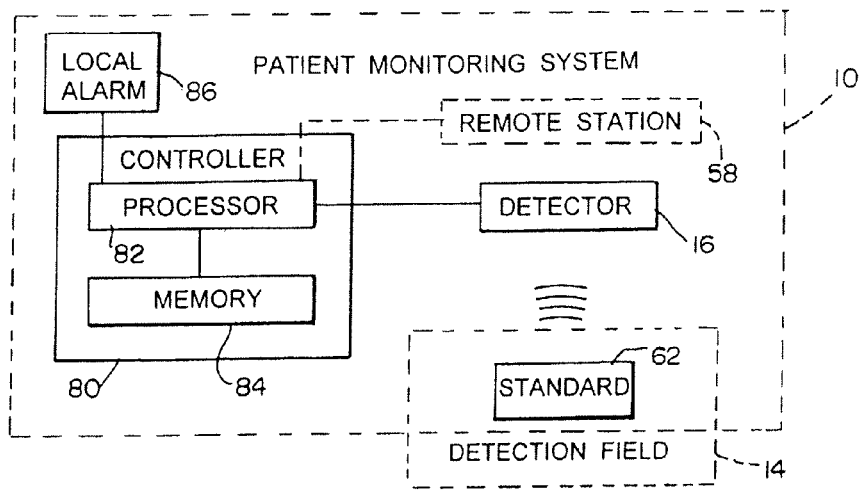
FIG. 6 is a diagrammatic representation of a patient-monitoring system.
Figure 7:
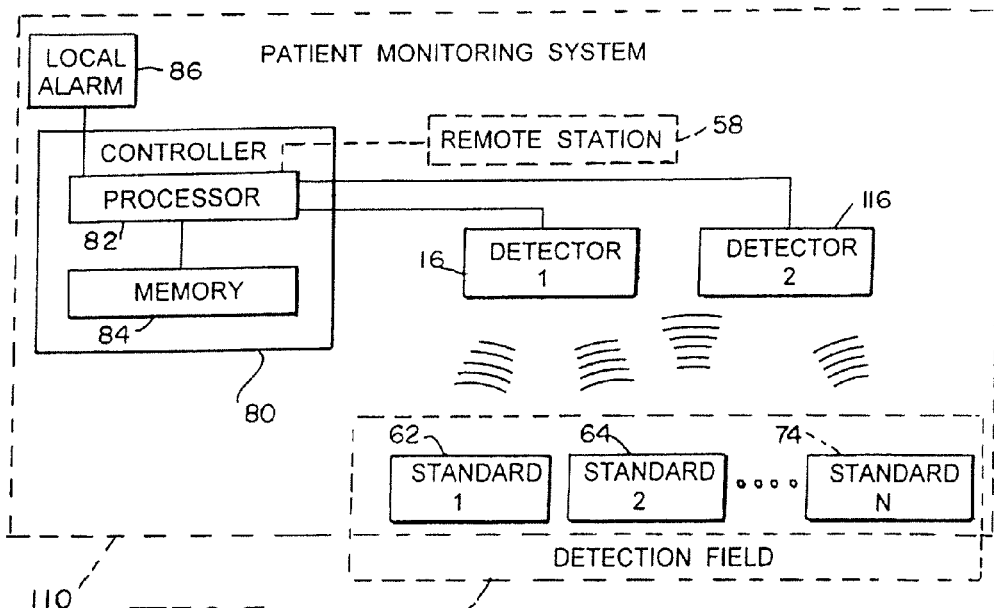
FIG. 7 is a diagrammatic representation of another embodiment of a patient-monitoring system.

As described earlier, the sensor 12 includes a detector 16. In the illustrative embodiment, the detector 16 is a charge coupled device (CCD) capable of receiving an image from the detection zone 14. In the illustrative embodiment, the detector 16 operates in the visible spectrum and compares an initial image of the patient 40 and patient-support apparatus 20 changes in the image over time to discern how a patient 40 has changed position over time. If the patient's position has changed sufficiently to indicate and unacceptable position, the system 10 will generate an alarm which may be visual or audible in the patient room 18, or it may be transmitted to a monitoring station 58 in the patient room 18 as indicated in FIGS. 6 and 7.

To detect movement of the patient 40, the system 10 must evaluate changes in a characteristic of the patient 40. Each person has a center of mass 60 which is generally located in the torso. According to the present disclosure, the center of mass 60 is estimated by determining the centroid of the portion of the patient 40 visible to the sensor 12. In one illustrative embodiment, the centroid 60 of the patient 40 is determined using geometric decomposition. The centroid of multiple simple shapes detected by the system 10 is first determined, and then the positions of each of the centroids of the simple shapes are averaged, weighted by the area of the simple shape used for each centroid. By continuously recalculating the centroid 60 of the patient 40, changes in the position of the centroid 60 may be used to determine if the patient 40 is properly positioned or is moving in a manner which indicates the patient 40 will attempt to exit the patient-support apparatus 20. In the visible spectrum, the analysis requires the system t10 to determine what in the detection zone 14 can be properly assigned to being a portion of the patient 40 and what in the view is environment. To overcome the difficulty in detecting the centroid 60 of an immobile patient 40, the system 10 may be taught the location of the centroid 60 by a user who positions a movable standard 74 on the patient's torso and synchronizing the position of the standard 74 with the system 10. The system 10 then monitors the area around the taught centroid 60 to determine if the patient 40 has moved relative to the fixed standards on the patient-support apparatus 20. In other embodiments, the movable standard 74 may be attached to the patient 40 so that movement of the patient 40 results in movement of the standard 74, which approximates the centroid of the patient 40.

In another embodiment, the detector 16 is configured to detect electromagnetic radiation in the infrared spectrum. This significantly simplifies the determination of the centroid 60 of the patient 40. In the infrared embodiment, the system 10 is configured to accept that any electromagnetic radiation in the field of view that indicates a temperature of greater than a predetermined threshold, such as 85° F., for example, is assumed associated with the patient 40. Once an area is sensed to be associated with the patient 40, a centroid 60 may be determined based simply on an average position of the areas associated with the patient 40. For additional accuracy, the centroid may be weighted by both position and temperature so that a heat based centroid may be determined. Movement of the centroid 60 of the patient 40 relative to the standards 62, 64, 66, 68, 70, and 72 is then monitored by the system 10 to monitor the patient's movement.

Figure 3:
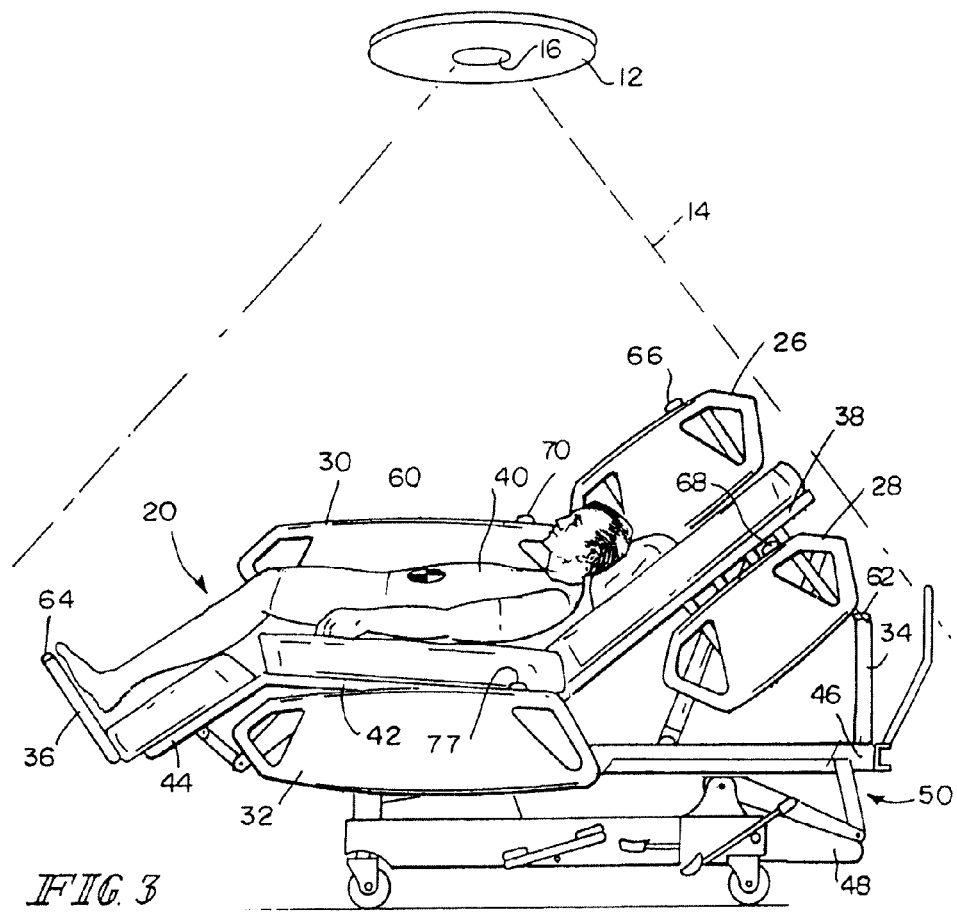
FIG. 3 is a perspective view similar to FIG. 1 with articulated sections of the patient-support apparatus moved to place the patient reclined position with the patient's head and knees raised.

In use, the system 10 may compare the position of the patient 40 to the standards 62, 64, 66, 68, 70, and 72 to determine that the patient 40 has moved to a position in which the patient 40 is at risk for injury. For example, in FIGS. 3 and 4, the patient 40 is shown to have migrated toward the foot-panel 36 so that the patient's back is being supported by the thigh section 42 and the patient 40 is in an improper position. For example, the centroid 60 of the patient 40 in FIGS. 3 and 4 is positioned outside of the polygon 54 and is spaced away from the polygon 54 by a distance Z. The system 10 may alert a caregiver that the patient 40 is out of position and should be re-positioned to the optimal position.

Figure 5:
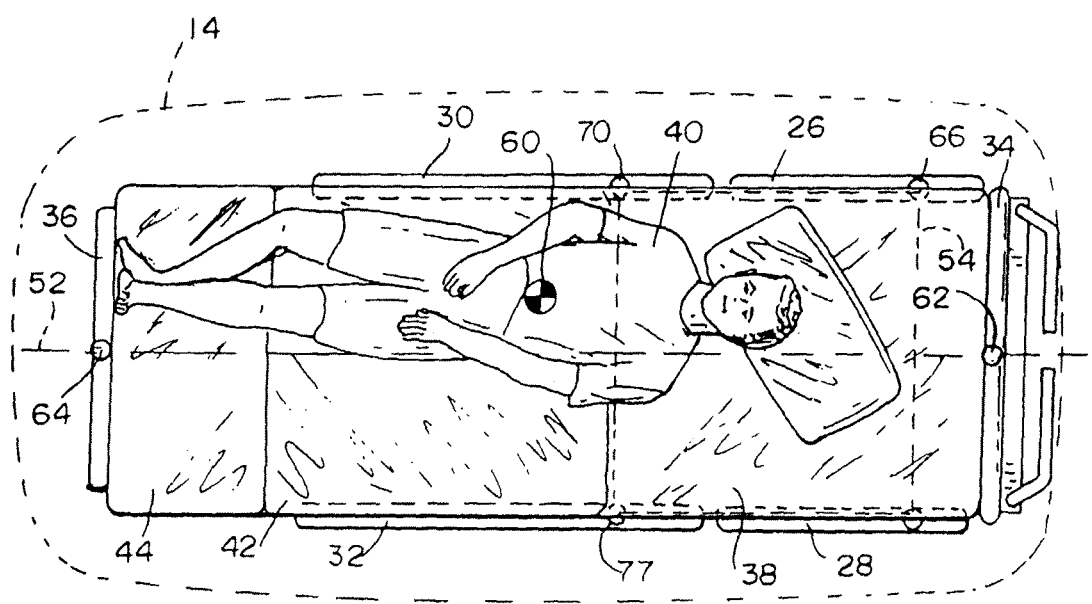
FIG. 5 is a top view similar to the top view of FIG. 2, with the patient in FIG. 5 shown positioned closer to the foot end of the patient-support apparatus.

Similarly, the patient 40 is shown to be migrated to the patient-right side of the patient-support apparatus 20 in FIG. 5. After determining that the centroid 60 is spaced apart from the axis 52, the system 10 may send signal indicative that the patient 40 is out of position, resulting in an alarm either in the room 18 or at the remote station 58. It should also be noted that the shape of the polygon 54 may be used to determine if one or more siderails 26, 28, 30, or 32 are in a lowered position. Again referring to FIG. 5, it is shown that when the patient-left head siderail 28 is in a lowered position and the head section 38 is raised, the polygon 54 has an irregular shape and the standard 68 is positioned closer to the head-panel 34 than the standard 66, thus indicating that the siderail 28 is in a lowered position.

While the forgoing description explains the use of multiple standards, it should be understood that the system 10 may detect positioning or movement of a patient 40 with respect to a single standard, such as standard 62, for example. In one embodiment, the standard 62 positioned on the headpanel 34 defines a fixed position and is indicative of an orientation defining the axis 52. Movement of the centroid 60 relative to the standard 62 and axis 52 provides sufficient information for the system 10 to determine if the patient 40 is moving relative to the patient-support apparatus 20 or if the patient 40 is in an unacceptable position such as that shown in FIGS. 3 and 4 or FIG. 5.

In another embodiment, a patient monitoring system 110 may include multiple detectors 16, 116 as shown in FIG. 7. Each of the detectors 16, 116 may be positioned in different known locations on the ceiling 22 with the detectors 16, 116 each configured to have the same detection zone 14. The system 110 may then process data from each of the detectors 16, 116, comparing the data from each of the different detectors 16, 116 to determine information about the patient 40 and position of the members of the patient-support apparatus 20. In some embodiments, one sensor 12 may have a detector 16 used to detect electromagnetic radiation in the visible spectrum and a second sensor 12 may have a detector 116 electromagnetic radiation in the visible spectrum to provide additional data on movement in the field of view 14. It should be understood that while the illustrative embodiment of FIG. 7 shows two detectors 16, 116, other embodiments may include additional sensors 12 each with an associated detector 16 with the system utilizing data from all of the sensors 12 to determine information about the patient 40 or patient-support apparatus 20 in the detection zone 14.

Each system 10, 110 includes at least one sensor 12, and one or more standards 62, 64, 66, 68, 70, and 72, and a controller 80. Each of the systems 10, 110 may optionally include a movable standard 74. The controller 80 includes a processor 82 and a memory device 84. The processor 82 utilizes data and algorithms stored in memory 84 to analyze data from the sensor 12 as described above. In some embodiments, the controller 80 will monitor the location of the patient 40 relative to the standards 62, 64, 66, 68, 70, and 72 so that the location of the patient 40 relative to the members of the patient-support apparatus 20 is monitored. In some embodiments, the controller 80 will indicate an alarm condition to a local alarm 86 positioned in the room 18. The local alarm 80 may provide either a visual indication of the alarm condition or an audible indication of the alarm condition, or both a visual and audible indication. The controller 80 may also provide a signal to the remote station 58 and the remote station 58 will generate an indication of the alarm condition at the location of the remote station 58. The remote station 58 is positioned apart from the patient room 18 so that a caregiver in a remote location is apprised of the alarm condition. The controller 80 may communicate with the local alarm 86 ore remote station 58 through either a hard-wired connection or a wireless connection. The remote station 58 may generate either an audible or visual indication of the alarm condition, or both an audible and visual indication.

In some embodiments, one of the standards 62, 64, 66, 68, 70, and 72 may provide a signal to the sensor 12 that is indicative of the specific patient-support apparatus 20 in the field 14. The sensor 12 may then identify the specific patient-support apparatus 20 identification to the remote station 58 such that a hospital information system in communication with the remote station 58 may associate the specific patient-support apparatus 20 to the specific room 18.

The system 10 may also monitor the standards 62, 64, 66, 68, 70, and 72 to determine the position of various members of the patient-support apparatus 20 and provide the position data to the hospital information system through the remote station 58. For example, the system 10 may monitor siderail position, bed elevation, articulated section positions, the amount of tilt of the intermediate frame. It should be understood that while the standards 62, 64, 66, 68, 70, and 72 are shown to be positioned on specific members of the patient-support apparatus 20 in the illustrative embodiment, other standards may be positioned on various members of the patient-support apparatus 20 such that one or more sensors 12 may monitor the location of the various standards, and thereby, members to monitor the position of the position of the members of the patient-support apparatus 20.

It is also contemplated that the system 10 may be used to monitor other characteristics of the patient 40 for vigilance monitoring. For example, by monitoring cyclical changes in position, the system 10 may monitor the respiration rate of a patient 40 on patient-support apparatus 20. Changes in the temperature profile of the patient 40 may also be used to detect incontinence of the patient. Still also, the system 10 may detect the patient's body temperature.

Although certain illustrative embodiments have been described in detail above, variations and modifications exist within the scope and spirit of this disclosure as described and as defined in the following claims.

The invention claimed is:

1. A monitoring system for monitoring a patient in a patient-support apparatus, the system comprising:
a first detector operable to detect electromagnetic radiation within a detection field, the detection field including a patient supporting area on the patient-support apparatus;
at least one standard configured to be supported on the patient-support apparatus for movement therewith, positioned in the detection field, the standard conveying electromagnetic radiation having a predetermined signature to the detector; and
a controller coupled to the detector, the controller including a processor and a memory device coupled to the processor; the memory device including instructions that, when executed by the processor, cause the controller to evaluate data received from the detector to compare all of the electromagnetic radiation in the detection field, including the patient supporting area, to the signature of the standard and determine if changes in the electromagnetic radiation are indicative of movement of a person in the detection field.

2. The monitoring system of claim 1, wherein the memory device further includes instructions that, when executed by the processor, cause the controller to output a signal if the changes in the electromagnetic radiation are indicative that movement of a person in the detection field exceeds a threshold value.

3. The monitoring system of claim 2, wherein the system further comprises a remote station that is spaced apart from the detection field and coupled to the controller, and wherein the signal is transmitted to the monitoring station.

4. The monitoring system of claim 3, wherein the electromagnetic radiation detected by the detector is in the visible spectrum.

5. The monitoring system of claim 3, wherein the electromagnetic radiation detected by the detector is in the infra red spectrum.

6. The monitoring system of claim 1, wherein the system further comprises a second detector operable to detect electromagnetic radiation within at least a portion of the detection field of the first detector, the second detector coupled to the controller, the memory device further including instructions that, when executed by the processor, compare electromagnetic radiation received by the second detector to electromagnetic radiation received by the first detector and to the signature of the standard to determine if changes in the electromagnetic radiation detected by the first detector are indicative of movement of a person in the detection field.

7. The monitoring system of claim 6, wherein the memory device further includes instructions that, when executed by the processor, cause the controller to output a signal if the changes in the electromagnetic radiation are indicative that movement of a person in the detection field exceeds a threshold value.

8. The monitoring system of claim 7, wherein the system further comprises a remote station that is spaced apart from the detection field and coupled to the controller, and wherein the signal is transmitted to the monitoring station.

9. The monitoring system of claim 8, wherein the electromagnetic radiation detected by the first detector is in the visible spectrum.

10. The monitoring system of claim 9, wherein the electromagnetic radiation detected by the second detector is in the infra red spectrum.

11. The monitoring system of claim 1, wherein the standard is a portable standard.

12. The monitoring system of claim 11, wherein the memory device includes instructions that, when executed by the processor, cause the system to determine a physical position of the portable standard to define a datum and changes in the electromagnetic radiation detected by the detector are compared to the datum to determine if the changes in the electromagnetic radiation are indicative of movement of a patient on the patient-support apparatus.

13. The monitoring system of claim 1, wherein the signature of the standard defines a datum and the system evaluates changes in electromagnetic radiation relative to the datum to determine if a patient on the patient-support apparatus has moved from an initial position.

14. The monitoring system of claim 1, wherein the system comprises a plurality of standards each having a predetermined signature and the memory device includes instructions that, when executed by the processor, cause the system to monitor changes in the position of the standards.

15. The monitoring system of claim 14, wherein the memory device includes instructions that, when executed by the processor, cause the system to determine if one or more of the plurality of standards is in an unacceptable position.

16. The monitoring system of claim 15, wherein the system generates a signal indicative of the unacceptable position and transmits the signal to a remote station spaced apart from the patient-support apparatus.

17. The monitoring system of claim 16, wherein the memory device includes instructions that, when executed by the processor, cause the system to evaluate the electromagnetic radiation to determine a location of a patient supported on the patient-support apparatus and to compare the location of the patient to the standards to determine if the patient is in an unacceptable position.

18. The monitoring system of claim 14, wherein the memory device includes instructions that, when executed by the processor, cause the system to evaluate the electromagnetic radiation to determine a location of a patient supported on the patient-support apparatus and to compare the location of the patient to the standards to determine if the patient is in an unacceptable position.

19. The monitoring system of claim 18, wherein the position of the patient is determined by determining a centroid of the patient.

20. The monitoring system of claim 19, wherein the centroid of the patient is determined by weighting components of the thermal profile of the patient to determine a thermally weighted centroid.

* * * * *